(12) United States Patent
Burbank et al.

(10) Patent No.: US 12,364,478 B2
(45) Date of Patent: *Jul. 22, 2025

(54) STAPLER CARTRIDGE WITH AN INTEGRAL KNIFE

(71) Applicant: Intuitive Surgical Operations, Inc., Sunnyvale, CA (US)

(72) Inventors: William A. Burbank, Sandy Hook, CT (US); Matthew A. Wixey, San Jose, CA (US); Nicholas Ragosta, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/407,962

(22) Filed: Jan. 9, 2024

(65) Prior Publication Data
US 2024/0138835 A1    May 2, 2024

Related U.S. Application Data

(63) Continuation of application No. 17/481,483, filed on Sep. 22, 2021, now Pat. No. 11,903,583, which is a
(Continued)

(51) Int. Cl.
*A61B 17/072*    (2006.01)
*A61B 90/00*    (2016.01)

(52) U.S. Cl.
CPC ............. *A61B 17/07207* (2013.01); *A61B 2017/07271* (2013.01); *A61B 2017/07278* (2013.01);
(Continued)

(58) Field of Classification Search
CPC .......... A61B 17/07207; A61B 17/0682; A61B 17/3211; A61B 2017/07271;
(Continued)

(56) References Cited

U.S. PATENT DOCUMENTS 5,389,098 A * 2/1995 Tsuruta ............ A61B 17/07207
606/49
5,632,432 A   5/1997 Schulze et al.
(Continued)

FOREIGN PATENT DOCUMENTS

CN    1732859 A    2/2006
CN    101028205 A    9/2007
(Continued)

OTHER PUBLICATIONS

Extended European search report for Application No. EP17860194.4, mailed on Jun. 3, 2020, 9 pages.
(Continued)

*Primary Examiner* — Robert F Long
(74) *Attorney, Agent, or Firm* — Farber LLC (57) ABSTRACT

Stapler cartridges and surgical apparatus that include a stapler cartridge can include a knife that retracts into the stapler cartridge after cutting stapled tissue to prevent an operator being cut by the knife during replacement of the used stapler cartridge with a new stapler cartridge. A stapler cartridge includes a staple pushing shuttle, a knife member slidably coupled with the staple pushing shuttle, and a cartridge body. The staple pushing shuttle is slidably coupled to the cartridge body. The cartridge body includes a guide track engaged by the knife member and configured so that a cutting blade of the knife member protrudes from the cartridge body during a first portion of a distal movement of the staple pushing shuttle and the cutting blade is retracted
(Continued)

into the cartridge body during a second portion of the distal movement of the staple pushing shuttle.

19 Claims, 6 Drawing Sheets

Related U.S. Application Data continuation of application No. 16/339,704, filed as application No. PCT/US2017/056075 on Oct. 11, 2017, now Pat. No. 11,147,552.

(60) Provisional application No. 62/406,845, filed on Oct. 11, 2016.

(52) U.S. Cl.
CPC .............. *A61B 2017/07285* (2013.01); *A61B 2090/0801* (2016.02)

(58) Field of Classification Search
CPC ........... A61B 2017/07278; A61B 2017/07285; A61B 2090/0801
USPC ........................................... 227/175.1–182.1
See application file for complete search history.

(56) References Cited

U.S. PATENT DOCUMENTS

| | | | |
|---|---|---|---|
| 5,673,840 A | 10/1997 | Schulze et al. | |
| 6,066,144 A | 5/2000 | Wolf et al. | |
| 8,167,898 B1 | 5/2012 | Schaller et al. | |
| 8,439,246 B1* | 5/2013 | Knodel | A61B 90/92 227/176.1 |
| 8,540,133 B2* | 9/2013 | Bedi | A61B 17/07207 227/19 |
| 8,556,151 B2 | 10/2013 | Viola | |
| 9,107,663 B2 | 8/2015 | Swensgard | |
| 9,498,215 B2* | 11/2016 | Duque | A61B 17/07207 |
| 9,743,928 B2 | 8/2017 | Shelton, IV et al. | |
| 10,105,142 B2* | 10/2018 | Baxter, III | A61B 17/105 |
| 10,111,665 B2 | 10/2018 | Aranyi et al. | |
| 10,335,147 B2* | 7/2019 | Rector | A61B 17/068 |
| 10,478,185 B2 | 11/2019 | Nicholas | |
| 10,610,223 B2* | 4/2020 | Wellman | A61B 17/07207 |
| 10,912,556 B2* | 2/2021 | Burbank | A61B 17/068 |
| 10,987,104 B2* | 4/2021 | Beardsley | A61B 17/072 |
| 11,147,552 B2 | 10/2021 | Burbank et al. | |
| 11,497,517 B2* | 11/2022 | Kostrzewski | A61B 17/00234 |
| 11,701,109 B2* | 7/2023 | Posey | A61B 17/072 227/180.1 |
| 11,903,583 B2 | 2/2024 | Burbank et al. | |
| 2004/0199180 A1* | 10/2004 | Knodel | A61B 17/07207 606/139 |
| 2004/0199181 A1* | 10/2004 | Knodel | A61B 17/07207 606/139 |
| 2005/0075657 A1* | 4/2005 | Bombard | A61B 17/1152 606/153 |
| 2007/0175950 A1 | 8/2007 | Shelton, IV et al. | |
| 2008/0167670 A1* | 7/2008 | Shelton | A61B 17/07207 606/167 |
| 2009/0206144 A1* | 8/2009 | Doll | A61B 17/07207 227/177.1 |
| 2010/0213241 A1* | 8/2010 | Bedi | A61B 17/07207 227/180.1 |
| 2011/0290851 A1* | 12/2011 | Shelton, IV | A61B 17/07207 227/176.1 |
| 2012/0104072 A1 | 5/2012 | Vidal et al. | |
| 2012/0215220 A1 | 8/2012 | Manzo et al. | |
| 2013/0048697 A1 | 2/2013 | Shelton, IV et al. | |
| 2013/0056522 A1 | 3/2013 | Swensgard | |
| 2013/0105545 A1 | 5/2013 | Burbank | |
| 2014/0005678 A1 | 1/2014 | Shelton, IV et al. | |
| 2014/0103093 A1 | 4/2014 | Koch, Jr. et al. | |
| 2014/0166725 A1* | 6/2014 | Schellin | B29C 43/00 227/178.1 |
| 2014/0166726 A1* | 6/2014 | Schellin | A61B 17/105 227/176.1 |
| 2014/0183244 A1* | 7/2014 | Duque | A61B 17/068 606/167 |
| 2014/0191015 A1* | 7/2014 | Shelton, IV | A61B 34/70 227/178.1 |
| 2015/0230794 A1 | 8/2015 | Wellman et al. | |
| 2015/0265275 A1 | 9/2015 | Chen et al. | |
| 2015/0374363 A1* | 12/2015 | Laurent, IV | A61B 17/105 227/176.1 |
| 2016/0058440 A1 | 3/2016 | Dinardo et al. | |
| 2016/0058441 A1* | 3/2016 | Morgan | A61B 17/0644 606/219 |
| 2016/0081690 A1* | 3/2016 | Baxter, III | A61B 17/105 227/180.1 |
| 2016/0166256 A1* | 6/2016 | Baxter, III | A61B 17/07207 227/176.1 |
| 2017/0245857 A1* | 8/2017 | Shelton, IV | A61B 17/068 |
| 2017/0303926 A1* | 10/2017 | Scheib | A61B 17/105 |
| 2018/0168593 A1 | 6/2018 | Overmyer et al. | |
| 2018/0235623 A1 | 8/2018 | Vendely et al. | |
| 2018/0344318 A1* | 12/2018 | Nicholas | A61B 17/07207 |
| 2019/0133579 A1 | 5/2019 | Duque et al. | |
| 2022/0071633 A1 | 3/2022 | Burbank et al. | |
| 2023/0051361 A1* | 2/2023 | Shelton, IV | A61B 34/00 |
| 2023/0113219 A1* | 4/2023 | Fernandes | A61B 17/0686 227/180.1 |

FOREIGN PATENT DOCUMENTS

| | | | |
|---|---|---|---|
| CN | 101584596 A | 11/2009 | |
| CN | 101626731 A | 1/2010 | |
| EP | 1813209 A1 | 8/2007 | |
| JP | H08336540 A | 12/1996 | |
| JP | 2004305740 A | 11/2004 | |
| JP | 2015532150 A | 11/2015 | |
| WO | WO-9529638 A2 * | 11/1995 | ........... A61B 17/064 |
| WO | WO-2013039821 A1 | 3/2013 | |
| WO | WO-2013063525 A1 | 5/2013 | |

OTHER PUBLICATIONS

International Search Report and Written Opinion for Application No. PCT/US2017/056075, mailed on Jan. 24, 2018, 14 pages (ISRG08860/PCT).
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP23191203. 1, mailed on Dec. 20, 2023, 11 pages.

* cited by examiner

STAPLER CARTRIDGE WITH AN INTEGRAL KNIFE

CROSS REFERENCE TO RELATED APPLICATION DATA

The present application is a continuation of U.S. patent application Ser. No. 17/481,483 filed Sep. 22, 2021, which is a continuation of U.S. patent application Ser. No. 16/339,704 filed Apr. 4, 2019, which is a 371 of International Application No. PCT/US2017/056075 filed Oct. 11, 2017, which claims the benefit of U.S. Provisional Application No. 62/406,845 filed Oct. 11, 2016. These applications are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. Reloadable stapling devices can be used in conjunction with these surgeries. Often, such devices have common features such as a knife for cutting stapled tissue following stapling of the tissue, with the knife translating from a proximal end to a distal end. Prior devices have used replaceable cartridges where the knife is integral to the surgical instrument, and the cartridge primarily houses staples. Hence, the knife is used with multiple stapling cartridges. The primary drawback to such designs is that the knife becomes duller with each use.

Other cartridge designs have a knife that is integral to the cartridge and disposed of along with the spent cartridge. This provides the advantage of a fresh knife for each stapling operation. However, to date, such prior designs are complex with respect to the knife and the knife driving mechanism, which may require the knife to be returned back to its starting position. Such designs can have undesirable failure modes. Thus, the cost and risk of using known knife-integral cartridges may be entirely prohibitive.

BRIEF SUMMARY

Embodiments disclosed herein relate to a stapling cartridge that includes an integral knife member. In some embodiments, a stapling cartridge includes a cartridge body and a staple pushing shuttle and knife assembly that is pushed from a proximal end of the cartridge body to a distal end of the cartridge body by an actuation assembly. In many embodiments, the staple pushing shuttle and knife assembly remains at the distal end and the actuation assembly is retracted and thereby separates from the staple pushing shuttle and knife assembly. In some embodiments, the knife member engages a guide track that restrains the knife member in a deployed cutting position relative to the staple pushing shuttle during a first segment of the movement from the proximal end to the distal end. Near the end of the movement from the proximal end to the distal end, the guide track is shaped to retract the knife member to a lower position (stowed position) relative to the staple pushing shuttle to retract the knife member within the cartridge body, thereby preventing accidental touching of the knife member after use. In many embodiments, because the knife member is integral to the stapling cartridge, the knife member is used once and then discarded with the stapling cartridge, thereby ensuring a sharp knife for each use. In contrast, in prior designs where the knife is integral to the surgical instrument instead of the replaceable stapling cartridge, the knife member can become comparatively dull after some number of uses. By retracting the knife to an unexposed stowed position at the distal end of the cartridge and retaining the staple pushing shuttle and knife member assembly at the distal end of the cartridge, the actuation mechanism can be simplified relative to an actuation mechanism that would return the knife back to the proximal end of the cartridge. Because the actuation mechanism can be simplified, the cost of the surgical instrument and/or the stapling cartridge can be reduced and the overall length of the stapling cartridge can be reduced, thereby enabling increased surgical access.

Thus, in one aspect, a stapler cartridge includes a staple pushing shuttle, a knife member, and a cartridge body. The knife member is slidably coupled to the staple pushing shuttle. The knife member includes a cutting blade and a first guide track engagement feature. The cartridge body has a proximal end and a distal end. The staple pushing shuttle is slidably coupled to the cartridge body. The cartridge body includes a plurality of openings at an upper surface for ejecting staples via a distal movement of the staple pushing shuttle. The cartridge body includes a first guide track engaged by the first guide track engagement feature. The first guide track is configured so that the cutting blade protrudes from the cartridge body during a first portion of the distal movement of the staple pushing shuttle and the cutting blade is retracted into the cartridge body during a second portion of the distal movement of the staple pushing shuttle.

In many embodiments of the stapler cartridge, the first guide track includes a section that induces the retraction of the cutting blade of the knife member into the cartridge body during the second portion of the distal movement of the staple pushing shuttle. For example, in many embodiments of the stapler cartridge, the first guide track includes a section inclined relative to the upper surface of the cartridge body to induce retraction of the cutting blade into the cartridge body.

In many embodiments of the stapler cartridge, the knife member is slidably mounted to the staple pushing shuttle. For example, in many embodiments of the stapler cartridge, the staple pushing shuttle includes a knife channel in which the knife member is slidably disposed.

In many embodiments of the stapler cartridge, the cartridge body includes a centrally disposed slot along which the knife member travels and a guide track on either side of the centrally disposed slot. Each of the guide tracks is engaged by the knife member to control the position of the knife member relative to the staple pushing shuttle throughout the distal movement of the staple pushing shuttle and the knife member. For example, in many embodiments of the stapler cartridge, the knife member further includes a second guide track engagement feature and the cartridge body further includes a second guide track. The second guide track engagement feature is disposed on an opposite side of the knife member relative to the first guide track engagement feature. The second guide track is engaged by the second guide track engagement feature and configured so that the cutting blade protrudes from the cartridge body during the first portion of the distal movement of the staple pushing shuttle and the cutting blade is retracted into the cartridge body during the second portion of the distal movement of the staple pushing shuttle.

In many embodiments of the stapler cartridge, the knife member slidably interfaces with opposite sides of a vertical rib of the staple pushing shuttle so as to stabilize the knife member relative to the staple pushing shuttle for all positions of the knife member relative to the staple pushing shuttle. For example, in some embodiments of the stapler cartridge, each of the first guide track engagement feature and the second guide track engagement feature protrude distally to interface with a vertical rib of the staple pushing shuttle to stabilize a position and/or an orientation of the knife member relative to the staple pushing shuttle. In some embodiments of the stapler cartridge, each of the first guide track engagement feature and the second guide track engagement feature slidingly interfaces with the vertical rib.

In many embodiments of the stapler cartridge, the staple pushing shuttle and the knife member remain at the distal end of the cartridge body after being moved from the proximal end of the cartridge body to the distal end of the cartridge body. For example, in some embodiments of the stapler cartridge, the cartridge body includes a retaining feature that retains the staple pushing shuttle at the distal end of the cartridge body. In some embodiments of the stapler cartridge, the retaining feature includes a flexible tab that engages the staple pushing shuttle to retain the staple pushing shuttle at the distal end of the cartridge body.

In many embodiments of the stapler cartridge, the cartridge body is pivotally mountable to an end effector. For example, in some embodiments of the stapler cartridge, the cartridge body includes an attachment feature proximate to the proximal end and configured to removably couple with an end effector that includes an upper jaw. In many embodiments of the stapler cartridge, the stapler cartridge forms a lower jaw of the end effector.

In another aspect, a surgical apparatus includes an elongated shaft, an end effector movably coupled to the shaft, and a stapler cartridge detachably mounted to the end effector. The end effector includes an upper jaw and a beam member. The beam member includes a first portion and a second portion. The first portion slidably interfaces with the upper jaw. The stapler cartridge forms a hinged lower jaw. The stapler cartridge includes a staple pushing shuttle, a knife member, and a cartridge body. The knife member is slidably coupled to the staple pushing shuttle. The knife member includes a cutting blade and a first guide track engagement feature. The cartridge body has a proximal end and a distal end. The staple pushing shuttle is slidably coupled to the cartridge body. The cartridge body includes a plurality of openings at an upper surface for ejecting staples via a distal movement of the staple pushing shuttle. The cartridge body includes a first guide track engaged by the first guide track engagement feature. The first guide track is configured so that the cutting blade protrudes from the cartridge body during a first portion of the distal movement of the staple pushing shuttle and the cutting blade is retracted into the cartridge body during a second portion of the distal movement of the staple pushing shuttle.

In many embodiments of the surgical apparatus, the first guide track includes a section that induces the retraction of the cutting blade of the knife member into the cartridge body during the second portion of the distal movement of the staple pushing shuttle. For example, in many embodiments of the surgical apparatus, the first guide track includes a section inclined relative to the upper surface of the cartridge body to induce retraction of the cutting blade into the cartridge body.

In many embodiments of the surgical apparatus, the knife member is slidably mounted to the staple pushing shuttle. For example, in many embodiments of the surgical apparatus, the staple pushing shuttle includes a knife channel in which the knife member is slidably disposed.

In many embodiments of the surgical apparatus, the cartridge body includes a centrally disposed slot along which the knife member travels and a guide track on either side of the centrally disposed slot. Each of the guide tracks is engaged by the knife member to control the position of the knife member relative to the staple pushing shuttle throughout the distal movement of the staple pushing shuttle and the knife member. For example, in many embodiments of the surgical apparatus, the knife member further includes a second guide track engagement feature and the cartridge body further includes a second guide track. The second guide track engagement feature is disposed on an opposite side of the knife member relative to the first guide track engagement feature. The second guide track is engaged by the second guide track engagement feature and configured so that the cutting blade protrudes from the cartridge body during the first portion of the distal movement of the staple pushing shuttle and the cutting blade is retracted into the cartridge body during the second portion of the distal movement of the staple pushing shuttle.

In many embodiments of the surgical apparatus, the knife member slidably interfaces with opposite sides of a vertical rib of the staple pushing shuttle so as to stabilize the knife member relative to the staple pushing shuttle for all positions of the knife member relative to the staple pushing shuttle. For example, in some embodiments of the surgical apparatus, each of the first guide track engagement feature and the second guide track engagement feature protrude distally to interface with a vertical rib of the staple pushing shuttle to stabilize a position and/or an orientation of the knife member relative to the staple pushing shuttle. In some embodiments of the surgical apparatus, each of the first guide track engagement feature and the second guide track engagement feature slidingly interfaces with the vertical rib.

In many embodiments of the surgical apparatus, the staple pushing shuttle and the knife member remain at the distal end of the cartridge body after being moved from the proximal end of the cartridge body to the distal end of the cartridge body. For example, in some embodiments of the surgical apparatus, the cartridge body includes a retaining feature that retains the staple pushing shuttle at the distal end of the cartridge body. In some embodiments of the surgical apparatus, the retaining feature includes a flexible tab that engages the staple pushing shuttle to retain the staple pushing shuttle at the distal end of the cartridge body.

In many embodiments of the surgical apparatus, the cartridge body is pivotally mountable to an end effector. For example, in some embodiments of the surgical apparatus, the cartridge body includes an attachment feature proximate to the proximal end and configured to removably couple with an end effector that includes an upper jaw. In many embodiments of the surgical apparatus, the stapler cartridge forms a lower jaw of the end effector.

The details of one or more implementations are set forth in the accompanying drawings and the description below.

Other features will be apparent from the description and drawings, and from the claims.

DETAILED DESCRIPTION

Figure 1:
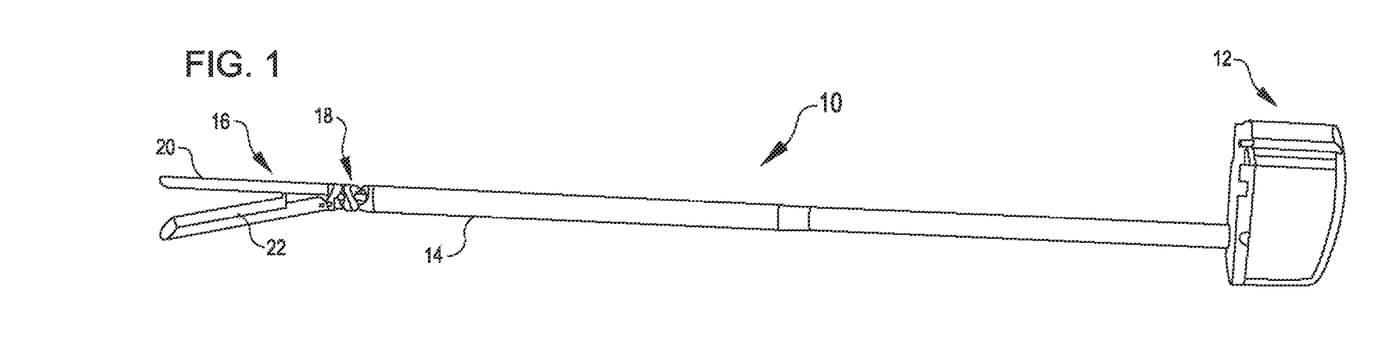
FIG. 1 shows a surgical tool, in accordance with some embodiments.

FIG. 1 shows a surgical tool 10 that includes a proximal chassis 12, an instrument shaft 14, a distal end effector 16 that can be articulated to grip tissue, and a wrist assembly 18. The proximal chassis 12 can include input couplers that can be interfaced with and driven by corresponding output couplers of a telesurgical surgery system, such as the system disclosed within Pub. No. US 2014/0183244 A1, which is incorporated by reference herein. The input couplers can be drivingly coupled with one or more actuation members that are disposed within the instrument shaft 14. The actuation members are drivingly coupled with the end effector 16.

The end effector 16 is moveably connected to the instrument shaft 14 by the wrist assembly 18. The wrist assembly 18 has at least two degree of freedom and provides for attachment of the end effector 16 to the elongated instrument shaft 14 for articulation of the end effector 16 about two orthogonal axes relative to the instrument shaft 14. The end effector 16 includes an upper jaw 20 and a lower jaw 22. The upper jaw 20 and/or the lower jaw 22 can be configured to articulate and grasp tissue. All or part of the lower jaw 22 take the form of a cartridge that can be removed from the end effector 16. The lower jaw 22 can house surgical staples for stapling cut tissue as well as a cutting mechanism that is housed solely within the cartridge.

Figure 2A:
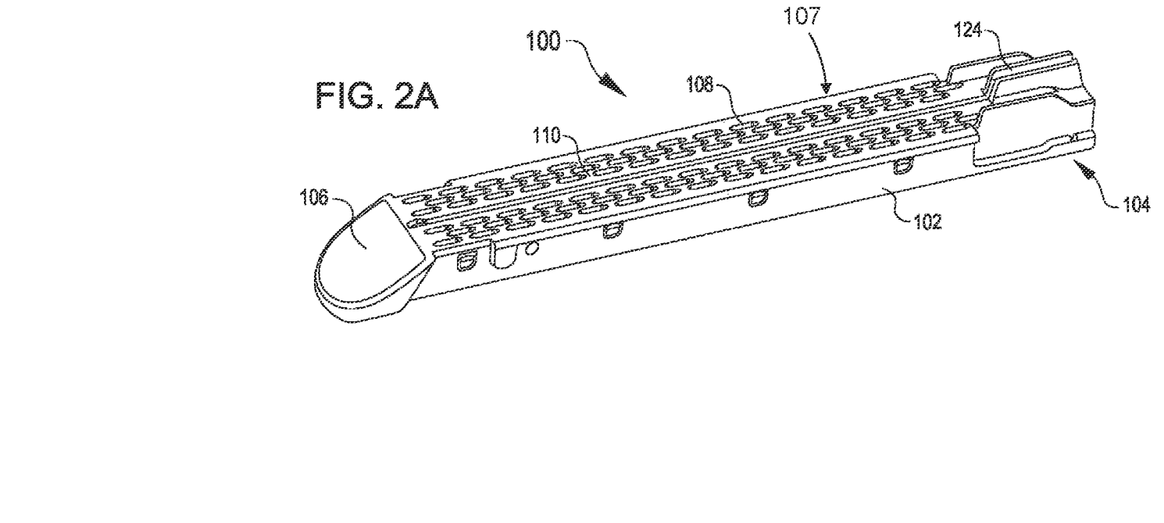
FIG. 2A shows a stapling cartridge, in accordance with some embodiments.

FIG. 2A shows a view of a cartridge 100, which can be used as the lower jaw 22 of surgical tool 10 or part of the lower jaw 22. The cartridge 100 is shown without some components for ease of description. The components of the cartridge 100 not shown in FIG. 2A are discussed below. The cartridge 100 has a cartridge body 102 with proximal end 104 that can be hingably coupled to the end effector 16 and a distal end 106 disposed at a corresponding distal end of the end effector 16. In some embodiments, the overall length of the cartridge 100 is greater than 45 mm, for example, over 60 mm. The cartridge body 102 includes a longitudinal slot 110 and multiple rows of staple openings 108 at an upper surface 107 of the cartridge body 102. In some embodiments, a staple is disposed in each of the staple openings 108 for deployment there from. The cartridge 100 can be configured to be the entire lower jaw 22, or in some embodiments attach to a framework of the lower jaw 22. In case of the latter, the cartridge body 102 can also include features adapted to be secured to holding features of the lower jaw 22.

Figure 2B:
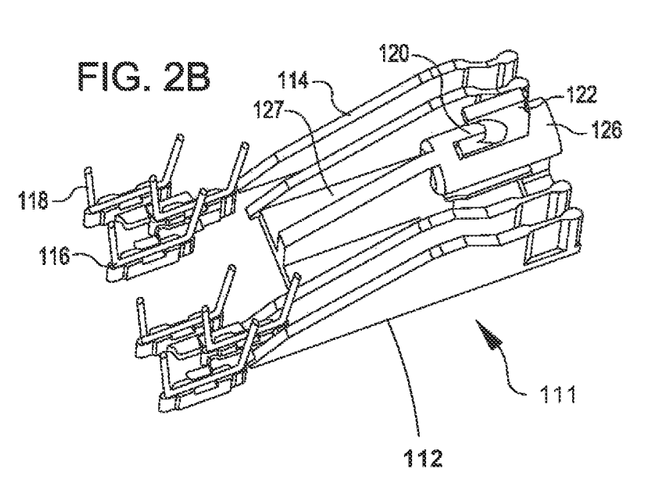
FIG. 2B shows a staple pushing shuttle and a knife member assembly of the stapling cartridge of FIG. 2A, in accordance with some embodiments.

FIG. 2B shows a view of a staple pushing shuttle and knife member assembly 111 that is housed within the cartridge body 102. The assembly 111 includes a staple pushing shuttle 112 and a knife member 122. The staple pushing shuttle 112 includes ramp portions 114 configured to interface with staple pushers 116, which in turn interface with staples 118. The staple pushing shuttle 112 slidingly interfaces with the cartridge body 102. Movement of the staple pushing shuttle 112 towards the distal end 106 of the cartridge body 102 results in engagement of the staple pushers 116 by the ramp portions 114 of the staple pushing shuttle 112 to drive the staple pushers 116 up relative to the cartridge body 102 to deploy the staples 118 out of the staple openings as the staple pushing shuttle 112 moves towards the distal end 106 of the cartridge body 102.

The staple pushing shuttle 112 includes a knife slot 120 that aligns with the longitudinal slot 110 of the cartridge body 102. The knife member 122 is slidingly disposed within the knife slot 120. The position of the knife member 122 within the knife slot 120 is controlled during a first portion of the movement of the staple pushing shuttle 112 from the proximal end 104 of the cartridge body 102 to the distal end 106 of the cartridge body 106 so that a cutting blade of the knife member 122 extends above the knife slot 120 and the longitudinal slot 110. At an initial, proximal position of the staple pushing shuttle and knife assembly 111, the knife member 122 is housed within a proximal garage 124 (shown in FIG. 3A and FIG. 3B) of the cartridge body 102. Both the knife slot 120 and the longitudinal slot 110 accommodate the cutting blade of the knife member 122 as the assembly 111 is moved toward the distal end 106 of the cartridge body 102 from the proximal garage 124. The staple pushing shuttle 112 also includes a guide member 126, which has a cylindrical outer surface in the illustrated embodiment. The guide member 126 provides a bearing surface that cooperates with a similarly shaped surface of the cartridge body 102, and hence guides movement of the staple pushing shuttle 112. The guide member 126 extends from a vertical rib member 127 of the staple pushing shuttle 112, which forms a central portion of the staple pushing shuttle 112 and provides a vertical interface for the knife member 122. The knife slot 120 is formed within the guide member 126 to help stabilize the knife member 122 during movement of the assembly 111.

In operation, the staples 118 are sequentially deployed starting at the cartridge proximal end 104 and proceeding to the cartridge distal end 106. In the illustrated embodiment, the knife member 122 is positioned distal to the ramp portions 114 of the staple pushing shuttle 112 so that only fully stapled tissue is cut. The knife member 122, or at least the cutting blade thereof, is retracted below the upper surface 107 of the cartridge body 102 prior to the assembly 111 reaching its distal most position adjacent to the distal end 106 of the cartridge body 102. With the cutting blade of the knife member 112 disposed below the upper surface 107 of the cartridge body 102 when the assembly 111 is at its distal most position, the cartridge 100 can be removed safely from the surgical tool without danger of the cutting blade of the knife member 122 cutting the operator. The retraction of the blade of the knife member 122 below the upper surface 107 is described in further detail below.

Figure 3A:
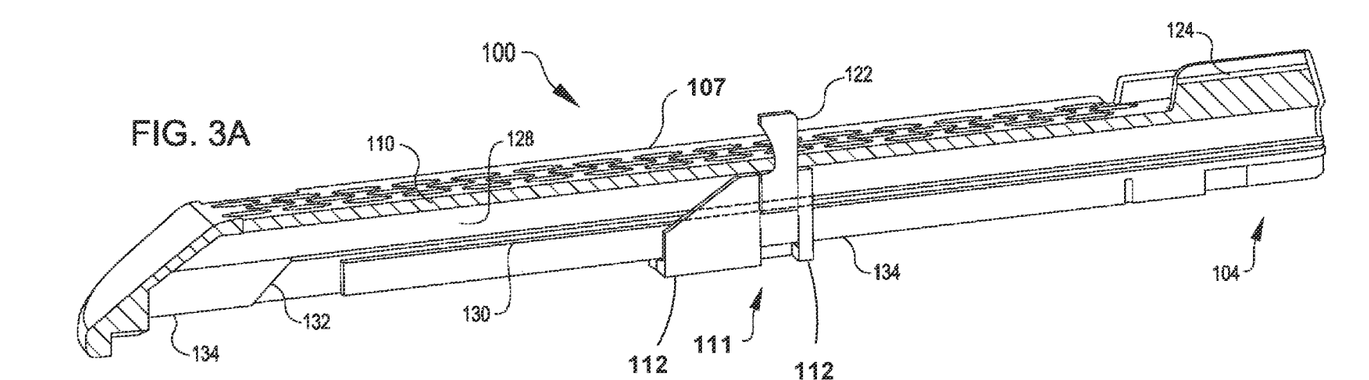
FIGS. 3A-3C show cross-sectional views of the stapling cartridge of FIG. 2A, in accordance with some embodiments.
Figure 3B:
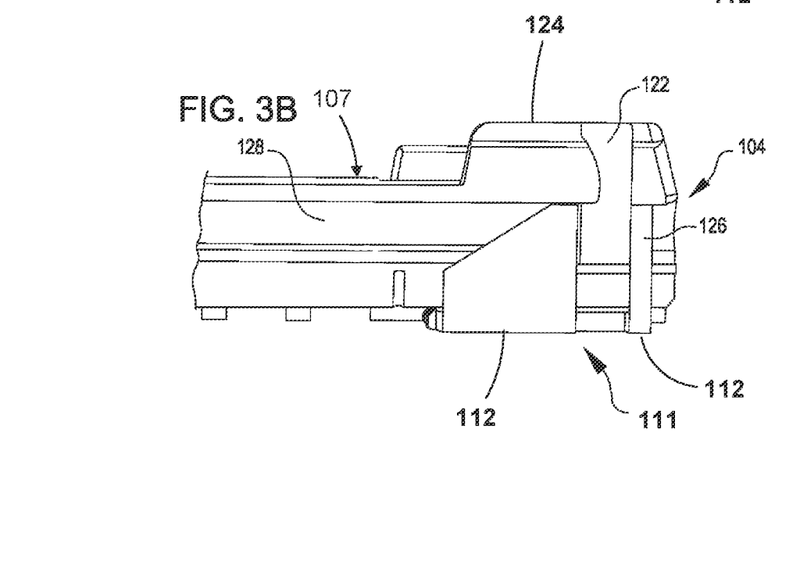
Figure 3C:
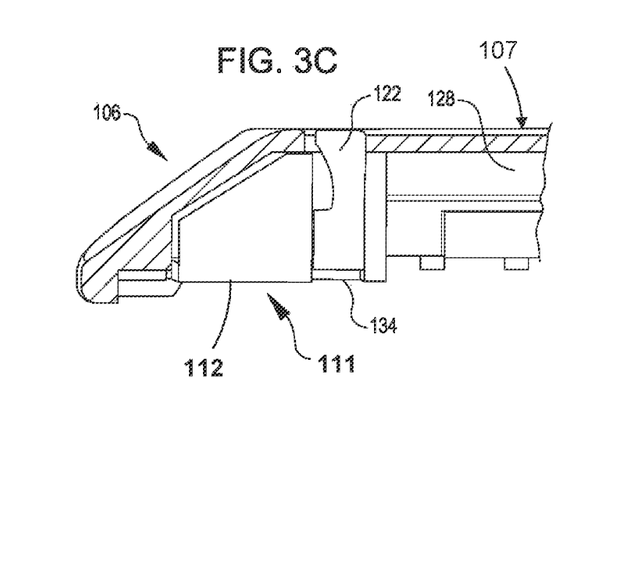

FIGS. 3A-3C depict cross-sectional views of the cartridge 100. As shown in FIG. 3B, the staple pushing shuttle and knife member assembly 111 is initially disposed at the proximal garage 124 with the knife member 122 protruding past the upper surface 107. At this position, the knife member 122 is concealed by the proximal garage 124 to prevent injury via contact with the knife member 122 during handling and installation of the cartridge 100. The guide member 126 of the staple pushing shuttle 112 is arranged to translate along an elongated lumen 128 formed within the cartridge body 102. The elongated lumen 128 has a circular profile to match the shape of the cylindrically shaped guide member 126. The profile of the guide member 126 and the elongated lumen 128, however, is not limited to being circular. Accordingly, the profile of the guide member 126 and the elongated lumen 128 can have any suitable shape, such as, for example, rectangular or hexagonal.

One or more sliding guide track engagement features (discussed in more detail below) of the knife member 122 are positioned to slide along one or more guide tracks formed within the cartridge body 102. In some embodiments, a first guide track is disposed on one side of the longitudinal slot 110. In some embodiments, a second guide track is disposed on the other side of the longitudinal slot 110. Each of the first guide track and the second guide track can have a first track segment 130. The first track segment 130 is elongated within the cartridge body 102 and extends along the elongated lumen 128. Generally, the first track segment 130 includes at least one bearing surface for a sliding guide track engagement feature of the knife member 122 to translate along. In some embodiments, the first track segment 130 extends from the proximal end 104 of the cartridge body 102 to a transition ramp 132 disposed near the distal end 106 of the cartridge body 102. In some embodiments, the first track segment 130 runs parallel to the upper surface 107. The transition ramp 132 joins the first track segment 130 to a second track segment 134 that is further away from the upper surface 107 than the first track segment 130. When the one or more sliding guide track engagement features engage the transition ramp 132 during the distal movement of the assembly 111, the knife member 122 is retracted to a position below the upper surface 107 as shown in FIG. 3C. In this retracted position, the knife member 122 is safely stowed such that the cartridge 100 can be safely removed from the surgical tool without danger the operator being cut by the knife member 122.

Figure 4A:
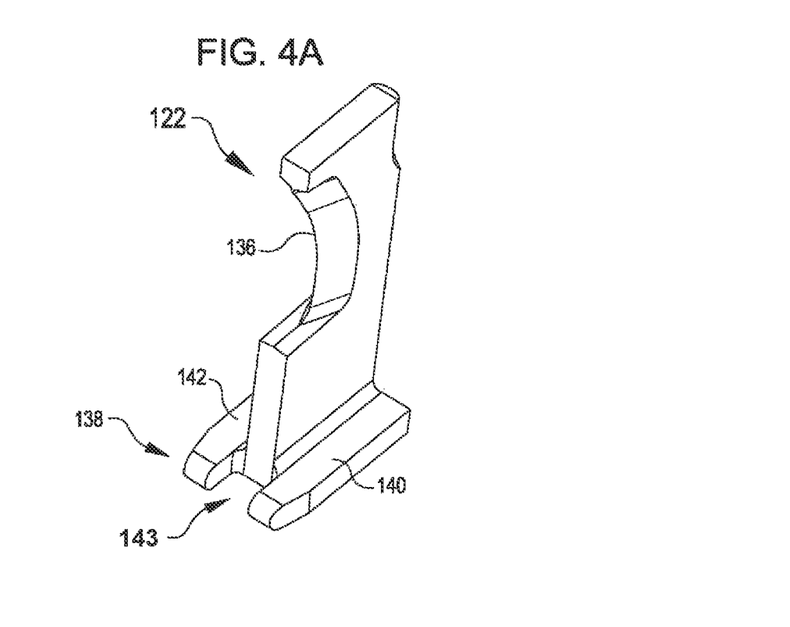
FIG. 4A shows the knife member of the staple pushing shuttle and knife member assembly of FIG. 2B.
Figure 4B:
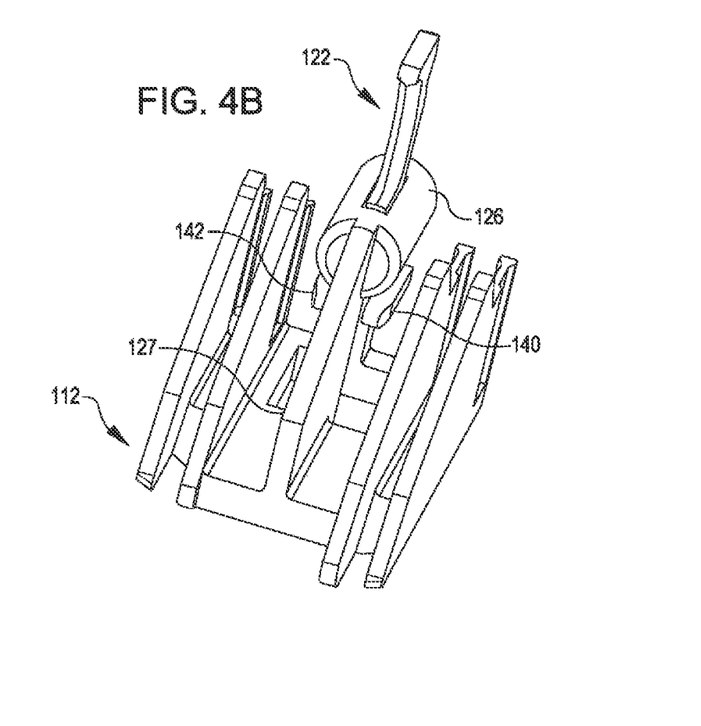
FIG. 4B shows the staple pushing shuttle and knife member assembly of FIG. 2B.

FIG. 4A shows a view of the knife member 122, which includes a cutting blade 136 for cutting tissue. The cutting blade 136 is arranged above a guide track engagement assembly 138 configured to slide along the first guide track and the second guide track. The guide track engagement assembly 138 includes a first guide track engagement feature 140 and a second guide track engagement feature 142. The first guide track engagement feature 140 and the second guide track engagement feature 142 share a common bottom surface and extend laterally from the knife member 122 to act as stops against the guide member 126, as shown in FIG. 4B. Each of the first guide track engagement feature 140 and the second guide track engagement 142 feature protrude distally to interface with a vertical rib 127 of the staple pushing shuttle 112 to stabilize a position and/or an orientation of the knife member 122 relative to the staple pushing shuttle 112. A distal separation between the first guide track feature 140 and the second guide track feature 142 defines a gap 143. The gap 143 accommodates the vertical rib 127 of the staple pushing shuttle 112 as the knife member 122 is moved relative to the staple pushing shuttle 112. In this manner, the gap 143 helps stabilize the knife member 122 during the distal movement of the assembly 111 and during the retraction of the knife member 122 below the upper surface 107 that occurs near the end of the distal movement of the assembly 111.

The distal movement of the assembly 111 and actuation of the lower jaw 22 is controlled by movement of a drive member 144, as depicted at FIGS. 5A-5D. The drive member 144 can be driven by an elongated and flexible cable that is housed within the shaft 14 of FIG. 1. The drive member 144 includes an upper flange 146 that is captured and slides within a rail feature 148 of the upper jaw 20. The drive member 144 also includes a lower flange 150 that cooperates with a bottom surface of the cartridge 100. Because the cartridge 100 is attached via a hinged connection, distal movement of the drive member 144 causes the lower flange 150 to forcibly cause the cartridge to actuate towards the upper jaw 20, which in some embodiments is fixed. The drive member 144 also pushes the assembly 111 in the distal direction to cause ejection of the staples 118 into tissue and an anvil surface of the upper jaw 20 to flatten the staples. Actuation of the assembly 111 by the drive member 144 also causes knife member 122 to move distally and cut stapled tissue.

Figure 5A:
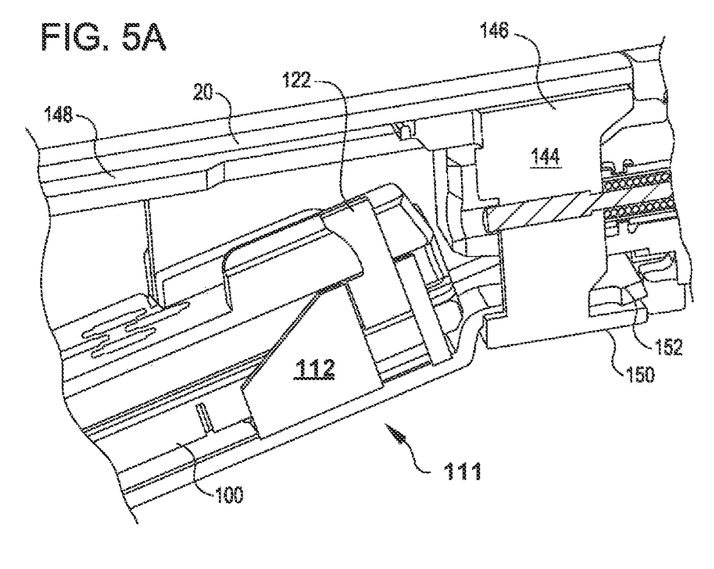
FIGS. 5A-5D shows cross-sectional views of the surgical tool of FIG. 1, in accordance with some embodiments.
Figure 5B:
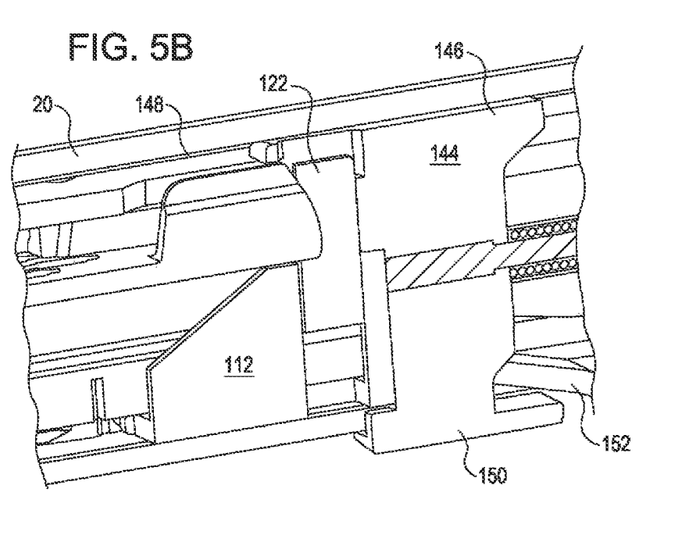
Figure 5C:
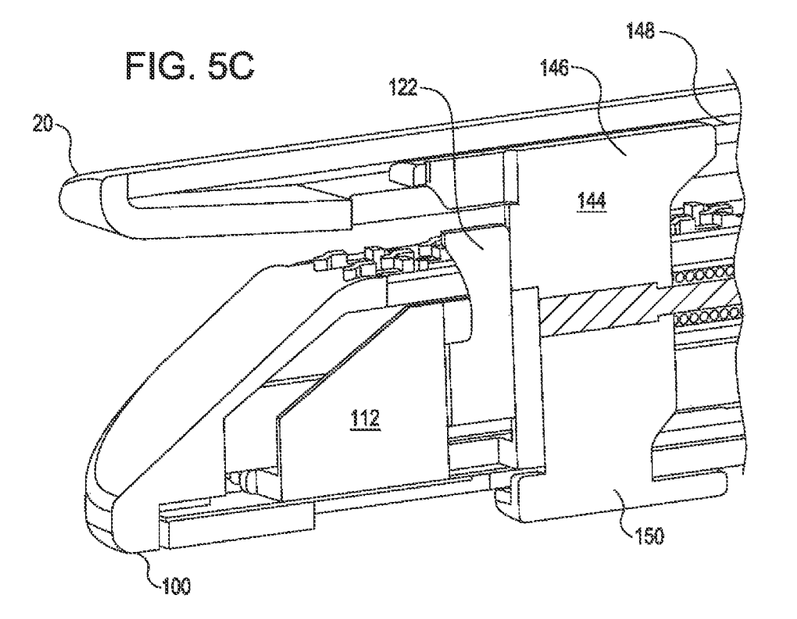

As shown in FIG. 5A, the cartridge 100 can be attached and removed from the surgical tool 10 by way of an elongated attachment feature 152 that is hingeably coupled below the upper jaw 20 and around the drive member 144. As shown in FIG. 5B, distal movement by the drive member 144 causes the lower flange 150 to move underneath the proximal portion of the cartridge 100 and forcibly actuate the cartridge 100 towards the upper jaw 20. Further distal movement of the drive member 144 further pushes the assembly 111 towards the distal end of the cartridge 100 to staple tissue and cut the stapled tissue until the assembly 111 reaches the position shown in FIG. 5C. In the configuration shown in FIG. 5C, the knife member 122 has been partially retracted via interaction of the guide track engagement assembly 138 with the transition ramp 134.

Figure 5D:
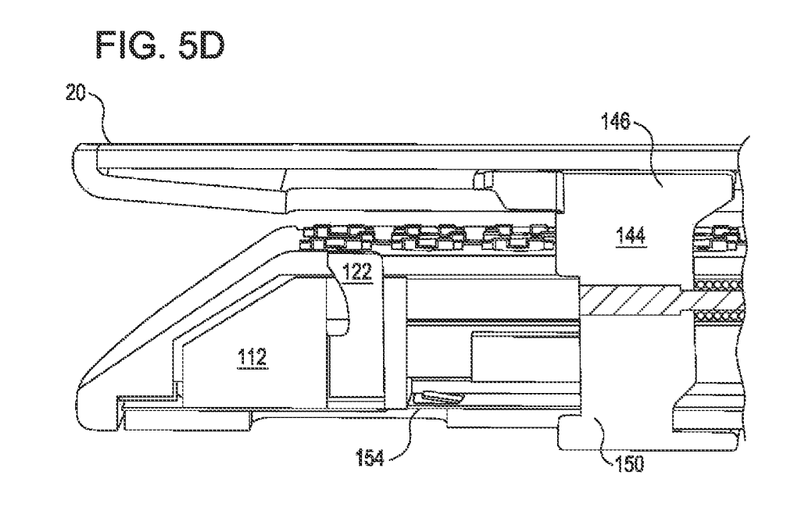

In the configuration shown in FIG. 5D, the assembly 111 has been advanced to a point that the knife member 122 has been retracted below the upper surface 107. The drive member 144 can then be retracted in the proximal direction to the configuration shown in FIG. 5A and the assembly 111 remains at the distal end. One or more retention features, such as a tab 154, can be used to retain the assembly 111 at the distal end of the cartridge 100. After the drive member 144 has been retracted proximally to a position that the drive member 144 no longer engages the lower surface of the cartridge 100, the cartridge 100 can then be removed and replaced with a new cartridge 100.

Other variations are within the spirit of the present invention. The various aspects, embodiments, implementations or features of the described embodiments can be used separately or in any combination. Various aspects of the described embodiments associated with operation of telesurgical tools can be implemented by software, hardware or a combination of hardware and software. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A surgical instrument comprising:
   an end effector having first and second jaws, at least one of the first jaws being movable between open and closed positions;
   a drive member configured to translate distally through the end effector; and
   a stapler cartridge comprising an upper surface, one or more staples, a cutting element, a slot for receiving the cutting element and a shuttle comprising one or more inclined ramps, wherein the cutting element is axially translatable relative to the shuttle in a direction substantially perpendicular to the slot; and
   a guide track configured to position the cutting element during a first portion of the distal movement of the drive member so that at least a portion of the cutting blade protrudes above the upper surface of the stapler cartridge and reposition the cutting element during a second portion of the distal movement of the drive member to retract the cutting element below the upper surface of the stapler cartridge.

2. The surgical instrument of claim 1, wherein the shuttle is slidably disposed within the stapler cartridge such that distal movement of the drive member causes distal movement of the shuttle.

3. The surgical instrument of claim 2, wherein the staple cartridge comprises a body having proximal and distal ends.

4. The surgical instrument of claim 1, wherein the cutting element comprises a blade and a guide track engagement feature that protrudes transversely relative to the slot and is engaged with the guide track.

5. The surgical instrument of claim 1, wherein the staple cartridge is removably coupled to the second jaw.

6. The surgical instrument of claim 3, wherein the shuttle comprises a guide portion configured to guide longitudinal translation of the shuttle relative to the stapler cartridge body.

7. The surgical instrument of claim 4, wherein the guide track is a first guide track and the cartridge body comprises a second guide track and the cutting element comprises a second guide track engagement feature engaged with the second guide track.

8. The surgical instrument of claim 7, wherein the second guide track is configured to position the cutting element during the first portion of the distal movement of the drive member so that the blade protrudes above the upper surface and reposition the cutting element within during the second portion of the distal movement of the drive member to retract the blade below the upper surface and at least partially into the second slot.

9. The surgical instrument of claim 3, wherein the shuttle is configured to constrain movement of the cutting element in a direction transverse to the upper surface of the stapler cartridge body.

10. A surgical instrument comprising:
    an end effector having first and second jaws, at least one of the first jaws being movable between open and closed positions;
    a stapler cartridge comprising a body, one or more staples, a cutting element, a slot for receiving the cutting element and a shuttle comprising one or more inclined ramps, wherein the cutting element is axially translatable relative to the shuttle in a direction substantially perpendicular to the slot;
    a drive member configured to translate the cutting element distally through the slot in the stapler cartridge; and
    wherein the cutting element is movable between a first position, wherein at least a portion of the cutting element protrudes from the stapler cartridge body, and a second position, wherein said portion of the cutting element is positioned within the stapler cartridge body.

11. The surgical instrument of claim 10, wherein said portion of the cutting element is a blade.

12. The surgical instrument of claim 10, wherein said portion of the cutting element retracts into the stapler cartridge body during distal translation of the drive member.

13. The surgical instrument of claim 10, wherein the cutting element is proximal of the one or more inclined ramps.

14. The surgical instrument of claim 13, wherein the cutting element moves into the second position after the staples have been deployed by the shuttle.

15. The surgical instrument of claim 13, wherein the cutting element remains in the first position before the staples have been deployed.

16. The surgical instrument of claim 13, wherein the cutting element is coupled to the shuttle such that distal translation of the shuttle causes distal translation of the cutting element.

17. The surgical instrument of claim 16, wherein the cutting element is configured to move in a transverse direction relative to a longitudinal axis of the surgical instrument between the first and second positions.

18. The surgical instrument of claim 17, wherein the cutting element is movable in a substantially perpendicular direction relative to the longitudinal axis.

19. The surgical instrument of claim 10, wherein the staple cartridge is removably coupled to the second jaw.

\* \* \* \* \*